United States Patent
Vinciguerra et al.

(10) Patent No.: US 6,315,771 B1
(45) Date of Patent: Nov. 13, 2001

(54) APPARATUS FOR CORNEAL SURGERY

(75) Inventors: Paolo Vinciguerra; Maurizio Sborgia, both of Milan (IT); Daniel Epstein, Langenthal (CH); Marco Azzolini, Milan (IT); Scott MacRae, Portland, OR (US)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/457,394

(22) Filed: Dec. 9, 1999

(51) Int. Cl.$^7$ ........................................ A61F 9/01
(52) U.S. Cl. ........................ 606/5; 606/10; 606/12; 606/13
(58) Field of Search ........................ 606/5, 10, 12, 606/13

(56) References Cited

U.S. PATENT DOCUMENTS

| | | |
|---|---|---|
| 5,445,633 | 8/1995 | Nakamura et al. . |
| 5,637,109 | 6/1997 | Sumiya . |
| 5,713,892 | 2/1998 | Shimmick . |
| 5,800,424 | 9/1998 | Sumiya . |

FOREIGN PATENT DOCUMENTS

| | | |
|---|---|---|
| 0 628 298 | 12/1994 | (EP) . |
| 6-327710 | 11/1994 | (JP) . |

OTHER PUBLICATIONS

P. Vinciguerra et al, "Photorefractive Keratectomy to Correct Myopic or Hyperopic Astigmatism With a Cross–cylinder Ablation," *J. Refract. Surg.*, vol. 15, pp. S183–S185 (Mar./Apr. 1999).

*Primary Examiner*—David M. Shay
(74) *Attorney, Agent, or Firm*—Finnegan, Henderson, Farabow, Garrett & Dunner, L.L.P.

(57) ABSTRACT

An apparatus for corneal surgery to correct a refractive error by ablating corneal tissue with a laser beam emitted from a laser source and delivered onto a cornea of a patient's eye with a light delivering optical system, the apparatus comprising an irradiation area limiting device for limiting an irradiation area of the laser beam and for varying the irradiation area, a first control device for controlling the irradiation area limiting device so as to reduce an ablation amount as the laser beam irradiates further away from a flattest meridian of astigmatism whereby effecting astigmatic correction, a second control device for controlling the irradiation area limiting device so as to increase an ablation amount as the laser beam irradiates further away from a steepest meridian of astigmatism whereby effecting astigmatic correction, and an arithmetic device for dividing a refractive power required for astigmatic correction into halves approximately equally so that an approximately half of the astigmatic correction is achieved by the first control device and the residual astigmatic correction is achieved by the second control device.

9 Claims, 3 Drawing Sheets

APPARATUS FOR CORNEAL SURGERY

BACKGROUND OF THE INVENTION

1. Field of the Invention

The present invention relates to an apparatus for corneal surgery to correct a refractive error by ablating corneal tissue with a laser beam, and more particularly to an apparatus suitable for astigmatic correction.

2. Description of Related Art

An apparatus for corneal surgery to correct an refractive error of an eyeball by ablating a corneal surface with an excimer laser is conventionally known.

However, astigmatic correction, especially myopic astigmatic correction, performed by using this kind of apparatus has a problem that is a hyperopic shift of spherical component often occurs after such a correction. To address this problem, two methods have been suggested: one is to minimize a size of ablation area in a meridian direction for correction so as to reduce affect of the hyperopic shift, and the other is to combine myopic astigmatic correction and hyperopic astigmatic correction in order to correct myopic astigmatism.

The latter method is to estimate a hyperopic shift of the spherical component which will be developed after the correction of the myopic astigmatism so as to combine ablation of each correction in consideration of the estimated hyperopic shift. For example, in the case where a hyperopic shift of 33% is estimated, upon correcting simple myopic astigmatism of which correction amount is S=0 D, C=−3.0 D and A=0°, 75% of the correction amount, that is C=−2.25 D and A=0°, is removed by ablation for myopic astigmatic correction. As the result, the hyperopic shift of 0.75 D, which accounts for 33%, occurs and the corneal refractive power after the ablation will be S=+0.75 D, C=−0.75 D and A=0°. Here, replacing the sign of the astigmatism with a plus sign, the residual correction amount will be S=0 D, C=+0.75 D and A=90°, which is equal to 25% of the correction amount to be corrected by ablation for hyperopic astigmatic correction.

Further, in the case of mixed astigmatism of which spherical equivalent is 0, 37% of the correction amount is achieved by myopic astigmatic correction and 63% is achieved by hyperopic astigmatic correction. For example, in the case where the correction amount is S=+2.0 D, C=−4.0 D and A=0°, by performing correction for S=0 D, C=−1.5 D and A=0° which is equal to 37% of the correction amount, C=−4.0 D in this case, a hyperopic shift of 0.5 D which accounts for 33% occurs and the resulting refractive power will be S=+2.5 D, C=−2.5 D and A=0°. Replacing the sign of the astigmatism with a plus sign, the residual correction amount will be S=0 D, C=+2.5 D and A=90°, which is equal to 63% of the correction amount to be corrected by hyperopic astigmatic correction.

In the former of the above methods, since the range (the size) where the correction is effected is narrow, there is a problem that the patient may experience halos or glare when, for example, the pupil has dilated at night.

The latter method has been suggested to address the problem arise in the former method. Yet, there is another problem that the hyper shift rate needs to be obtained as an empirical value to estimate hyper shift of the spherical component caused by myopic astigmatic correction. In addition, this method has been applied only for correction of a certain limited range.

SUMMARY OF THE INVENTION

The present invention has been made in view of the above circumstances and has an object to overcome the above problems and to provide an apparatus for corneal surgery which eliminates the need to obtain the hyper shift rate caused by astigmatic correction as an empirical value, and which can reduce adverse effect of change in the spherical component without a specific limitation on a corrective range upon astigmatic correction.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an apparatus for corneal surgery to correct a refractive error by ablating corneal tissue with a laser beam emitted from a laser source and delivered onto a cornea of a patient's eye with a light delivering optical system, the apparatus comprises irradiation area limiting means for limiting an irradiation area of the laser beam and for varying the irradiation area, first control means for controlling the irradiation area limiting means so as to reduce an ablation amount as the laser beam irradiates further away from a flattest meridian of astigmatism whereby effecting astigmatic correction, second control means for controlling the irradiation area limiting means so as to increase an ablation amount as the laser beam irradiates further away from a steepest meridian of astigmatism whereby effecting astigmatic correction, and arithmetic means for dividing a refractive power required for astigmatic correction into halves approximately equally so that an approximately half of the astigmatic correction is achieved by the first control means and the residual astigmatic correction is achieved by the second control means.

In another aspect of the present invention, an apparatus for corneal surgery to correct a refractive error by ablating an optical zone of a cornea with a laser beam, the apparatus comprises input means utilized for inputting each data necessary for correction, an optical system, first control means for controlling the optical system so as to bring a longitudinal axis of the slit aperture into coincidence with a flattest meridian of astigmatism whereby gradually changing the slit width of the slit aperture so that the laser beam that passes through the circular aperture and the slit aperture ablates more amount as it is closer to the flattest meridian and less amount as it is farther from the flattest meridian, second control mean for controlling the optical system in a manner that a longitudinal axis of the slit-like laser beam in a rectangular shape, which is limited by the circular aperture, is made parallel to a steepest meridian of astigmatism whereby gradually changing an eccentricity amount of the laser beam so that the laser beam that passes through the circular aperture and the slit aperture ablates less amount as it is closer to the steepest meridian and more amount as it is farther from the steepest meridian, and arithmetic means for dividing amount of astigmatic correction into halves approximately equally on the basis of the inputted data so that an approximately half of the astigmatic correction is achieved by the first control means and the residual astigmatic correction is achieved by the second control means. The optical system includes a circular aperture of which opening diameter is variable, a slit aperture of which slit width is variable, a projection lens for projecting the apertures onto the cornea, a moving unit for making an area irradiated by the laser beam eccentric with respect to a center of the optical zone, and a rotator for rotating the laser beam.

Further, in another aspect of the present invention, an apparatus for corneal surgery apparatus to correct a refractive error by ablating an optical zone os a cornea with a laser beam, the apparatus comprises input means utilized for inputting each data necessary for correction, an optical system, first control means for controlling the optical system in a manner that the scan mirror makes the laser beam in the rectangular shape scan an area limited by the circular aperture having a diameter larger than that of the optical zone and by the slit aperture of which longitudinal axis is brought into coincidence with a flattest meridian of astigmatism whereby gradually changing the slit width of the slit aperture after each scan, second control means for controlling the optical system in a manner that a longitudinal axis of the laser beam in the rectangular shape, which is limited by the circular aperture having a diameter larger than that of the optical zone, is made parallel to a steepest meridian of astigmatism whereby gradually changing an eccentricity amount of the laser beam with respect to the steepest meridian by the scan mirror so that the laser beam ablates more amount as it is farther from the steepest meridian, and arithmetic means for dividing amount of astigmatic correction into halves approximately equally on the basis of the inputted data so that an approximately half of the astigmatic correction is achieved by the first control means and the residual astigmatic correction is achieved by the second control means. The optical system includes a circular aperture of which opening diameter is variable, a slit aperture of which slit width is variable, a projection lens for projecting the apertures onto the cornea, a scan mirror for making the laser beam in a rectangular shape in a manner that it crosses the opening of the circular aperture or slit aperture, and an image rotator for rotating the laser beam on an optical axis of the optical system.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

A detailed description of one preferred embodiment of an apparatus for corneal surgery embodying the present invention will now be given referring to the accompanying drawings.

Figure 1:
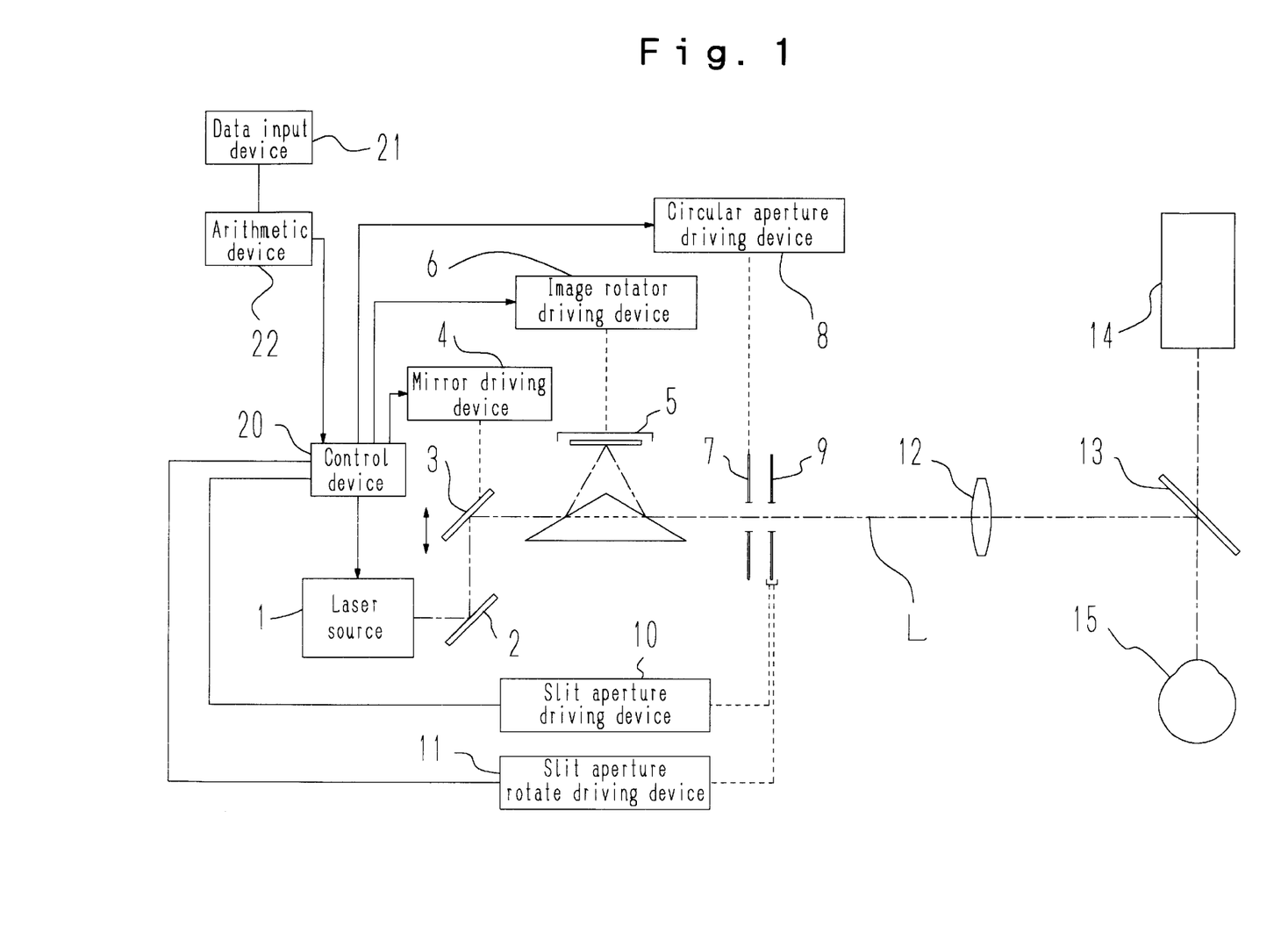
FIG. 1 is a view showing a schematic configuration of an apparatus for corneal surgery according to the present invention.

FIG. 1 is a view showing a schematic configuration of the apparatus for corneal surgery of the present invention.

Reference numeral 1 is a laser source and used in this embodiment is an excimer laser whose wavelength is 193 nm. A laser beam which is emitted from the laser source 1 is pulsed light of which typical shape is as follows. The intensity distribution of the beam shows almost uniform distribution in a horizontal direction, and Gaussian distribution in a vertical direction. Further, the laser beam has a slim rectangle cross-sectional shape when taken along an orthogonal plane relatives to an optical axis L. This is shaped into an intended shape by beam shaping means such as an expander lens as necessary.

The laser beam emitted from the laser source 1 is deflected upward by a plane mirror 2, then into a horizontal direction by a plane mirror 3. The plane mirror 3 is movable by a mirror driving device 4 in the direction of the arrow shown in FIG. 1 so as to move the laser beam in parallel to the direction of the Gaussian distribution for effecting uniform ablation of an object.

5 is an image rotator which is rotated on the optical axis L by an image rotator driving device 6 so as to rotate the laser beam on the optical axis L. 7 is a variable circular aperture which limits an ablation region. The opening region of the circular aperture 7 is changed by a circular aperture driving device 8. 9 is a variable slit aperture which limits the ablation region to a slit shape and can change the opening width by a slit aperture driving device 10. Further, the slit aperture 9 is rotated on the optical axis L by a slit aperture rotate driving device 11 so that the direction of the slit opening may be changed. The slit aperture 9 is used when correcting myopic astigmatism and the like.

12 is a projection lens to project the circular aperture 7 and the slit aperture 9 on a cornea 15 of a patient's eye. The region, which is restricted by the circular aperture 7 and the slit aperture 9 forms an image on the cornea 15.

13 is a dichroic mirror has a characteristic of reflecting the excimer laser beam of 193 nm and transmitting visible light. After passing through the projection lens 12, the laser beam is reflected by the dichroic mirror 13 and directed onto the cornea 15. 14 is an observation optical system comprising a binocular operation microscope (a commercially available one may be used) is positioned above the dichroic mirror 13. The patient's eye is preliminary positioned at a predetermined position upon an operation and kept the positioning state by watching a not illustrated fixation light.

21 is a data input device for inputting required data to correct the patient's eye. 22 is an arithmetic device for obtaining a required ablation amount on the basis of the inputted data.

20 is a control device for controlling the laser source 1 as well as each of the driving devices 4, 6, 8, 10 and 11 to correct the required ablation amount obtained by the arithmetic device 22.

Next, descriptions are given briefly and separately to ablation for the myopic correction, hyperopic correction, myopic astigmatic correction, hyperopic astigmatic correction by controlling drive of the plane mirror 3, the image rotator 5, the circular aperture 7 and the silt aperture 9.

Myopic Correction

In the case of performing myopic correction, the ablation region is limited with the circular aperture 7 and the laser beam is moved in a direction of the Gaussian distribution by moving the plane mirror 3 step by step. After the laser beam sweeps along one plane (one scanning), by rotating the image rotator 5, the moving direction of the laser beam is changed (for example, into three directions at 120° intervals therebetween), thereby to ablate the exposed area limited with the circular aperture 7 approximately uniformly. By repeating this procedure with a different opening size of the circular aperture 7, which is changed in a stepwise fashion, the cornea is ablated deeper at the center and less at the periphery (see U.S. Pat. No. 5,637,109 for detail).

Hyperopic Correction

In the case of performing hyperopic correction, the circular aperture 7 limits the ablation region with the opening region thereof being fixed. The plane mirror 3 is made shifted with respect to the optical axis L thereby to shift the path of the laser beam, and the image rotator 5 is made rotate so as to ablate the cornea in an annular shape. As the plane mirror 3 moves stepwise and therefore the shift amount of the laser beam from the optical axis L becomes greater, the number of the irradiation pulses (the irradiation time) is increased. As the result, the cornea is ablated at a relatively shallow depth at the center and at a deeper depth at the periphery for effecting hyperopic correction. The thus obtained refractive power is controlled by changing the total number of the irradiation pulses while keeping the same proportion among the number of the irradiation pulses at each point where the laser beam is shifted from the optical axis L due to the movement of the plane mirror 3 (see U.S. Pat. No. 5,800,424 for the detail).

Hyperopic Astigmatic Correction

In the case of performing hyperopic astigmatic correction, the circular aperture 7 limits the ablation region with the opening region thereof being fixed, and the plane mirror 3 is moved stepwise so as to move the laser beam in a direction of the Gaussian distribution. At that time, the image rotator 5 is rotated to adjust the moving direction of the laser beam shaped into a slit-like (rectangular) shape so that the laser beam moves in a direction of the flattest meridian of astigmatism (the image rotator 5 is rotated to adjust so that a longitudinal axis of the slit-like laser beam in a rectangular shape is made parallel to the steepest meridian of astigmatism). The laser beam is moved stepwise with the number of the irradiation pulses at each point increased in a suitable ratio as the laser beam shifted to the periphery. As the result, the cornea is ablated at a relatively shallow depth at the center and at a deeper depth at the periphery (see U.S. Pat. No. 5,800,424 for the detail).

Myopic Astigmatic Correction

In the case of performing myopic astigmatic correction, the opening region of the circular aperture 7 is fixed, and the opening width of the slit aperture 9 is changed. In addition, the slit aperture 9 is adjusted its direction of the slit by the slit aperture rotate driving device 11 so that the opening width changes in a direction of the steepest meridian of astigmatism (the slit aperture 9 is adjusted its direction of the slit so as to bring a longitudinal axis of the slit aperture 9 into coincidence with the flattest meridian of astigmatism). The laser beam irradiation is carried out in the same manner as the myopic correction. That is, the laser beam is made move in a direction of the Gaussian distribution by moving the plane mirror 3 stepwise, and after each scan of the laser beam, the moving direction of the laser beam is changed by the rotation of the image rotator 5. As the result, the range limited by the circular aperture 7 and the slit aperture 9 is ablated approximately uniformly. By repeating this procedure with a different opening width of the slit aperture 9, which is changed stepwise, ablation is done in a manner to flatten the cornea in a direction of the steepest meridian.

Further, it is also possible to increase the number of the irradiation pulses, as in the case of hyperopic astigmatic correction, at each point where the laser beam moves stepwise but in a reverse way: the number of the irradiation pulses is increased as the laser beam irradiates a closer point to the center (see U.S. Pat. No. 5,800,424 for the detail).

Description is now given to ablation for astigmatic correction according to the present invention.

There have been cases where data indicating partial overcorrection is found upon checking a corneal topography map after performing myopic astigmatic correction alone by using a slit aperture and the like. Therefore, simple simulations were carried out.

Figure 2:
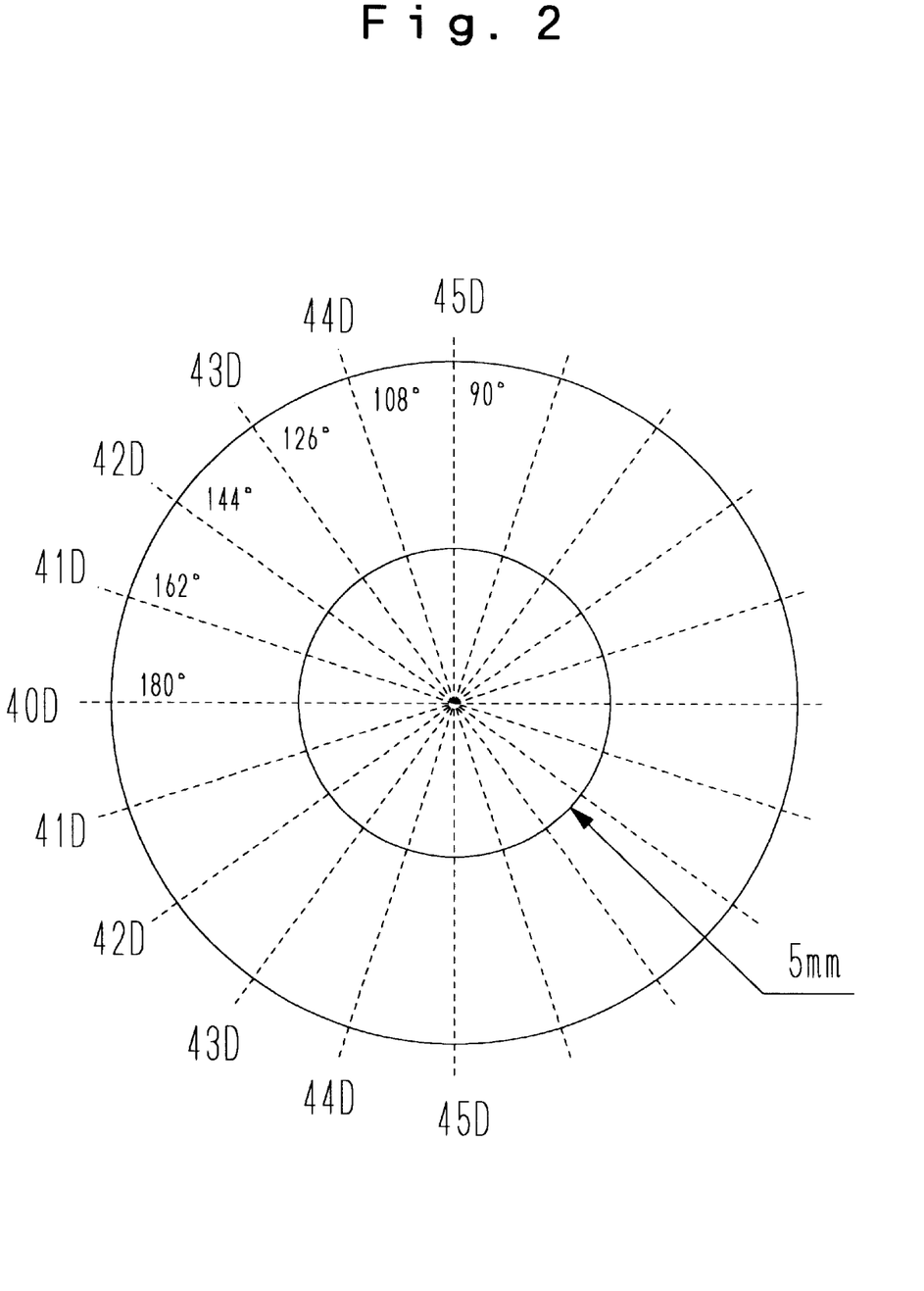
FIG. 2 is a view showing an example of distribution of a corneal refractive power that is used in a simulation of astigmatic correction.
Figure 3:
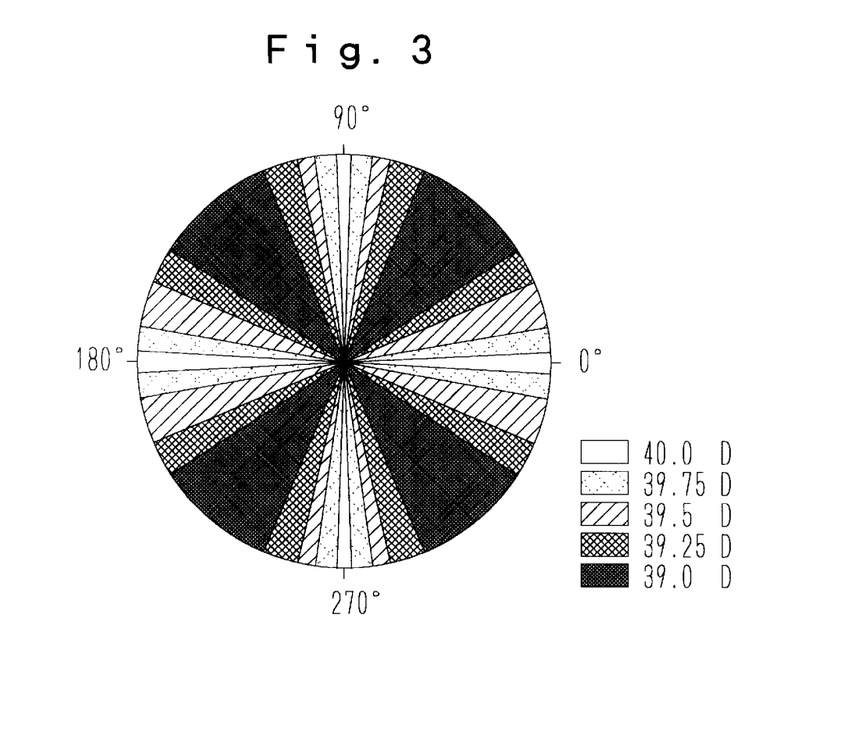
FIG. 3 is a view showing a refractive power obtained as a result of a simulation of myopic astigmatic correction performed on the cornea shown in FIG. 2.

As shown in FIG. 2, a cornea has a preoperative refractive power is 45 D in a 90° direction and 40 D in a 180° direction. A simple simulation was carried out on this cornea to see a postoperative refractive power along each meridian induced by ablation on a zone of 5 mm in a manner to remove a cylindrically shaped portion having an astigmatism power (cylindrical power) C=−5.0 D, an angle of astigmatic axis A=180° thereby to reshape the cornea into a spherical shape. It is clear from the result, as shown in FIG. 3, that there are portions being overcorrected in a certain pattern. This is considered to be the factor, after performing myopic astigmatic correction which ablates deeper at the center and less at the periphery in the steepest meridian direction, that causes hyperopic shift of the spherical component and under correction of the astigmatic component.

Figure 4:
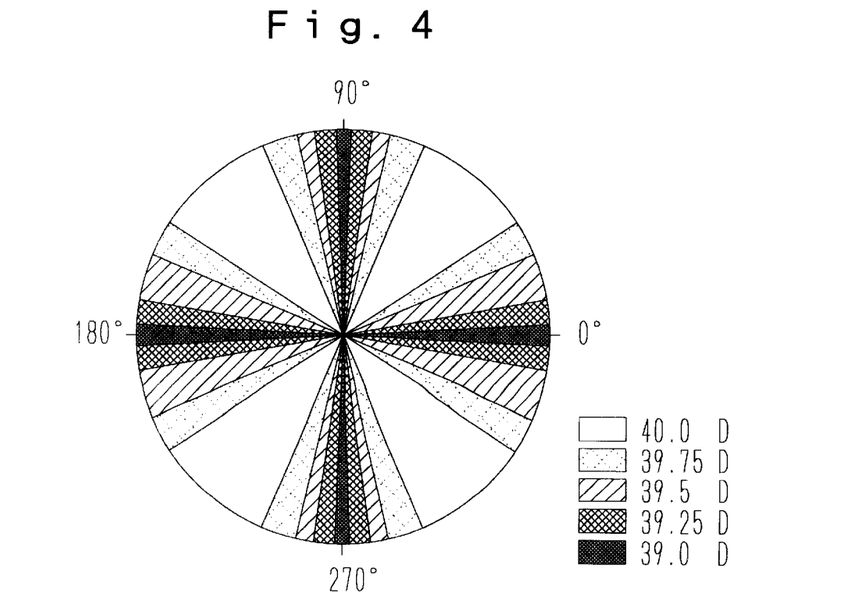
FIG. 4 is a view showing a refractive power obtained as a result of a simulation of hyperopic astigmatic correction performed on the cornea shown in FIG. 2.

In addition, another simulation was performed on the cornea having the same refractive power as stated above to see a postoperative refractive power in a direction of each meridian after performing hyperopic astigmatic correction to ablate a cylindrical shaped portion having an astigmatism power C=+5.0 D, an angle of astigmatic axis A=90° thereby to reshape the cornea into a spherical shape. It is clear from the result as shown in FIG. 4, there are portions of undercorrection, contrary to the case of myopic astigmatic correction, in a similar pattern.

Here, in the present invention, a step of hyperopic astigmatic correction and a step of myopic astigmatic correction are performed in combination to correct astigmatism, and upon combining the two steps, the amount of the astigmatic correction are divided into halves (equal power). (It does not have to be divide strictly equally in practice.) The combination eliminates adverse effects of each correction allowing to reshape a cornea into a perfectly spherical shape. Thereafter, by performing a step of spherical correction (the above-mentioned myopic or hyperopic correction) for the spherical equivalent of corrective refractive power, the residual correction may be effected.

That is, letting S denote spherical power of the corrected refractive power, and C denote the astigmatism power (taken with a minus sign), and A denote an angle of an astigmatic axis, then an amount to be corrected in each step is calculated as follows:

(1) First step (hyperopic astigmatic correction),
$S_1=0$, $C_1=-C/2$, $A_1=A+90$ ($A=0°\sim90°$) or $A_1=A-90$ ($A=91°\sim180°$)

(2) Second step (myopic astigmatic correction),
$S_2=0$, $C_2=C/2$, $A_2=A$; and (3) Third step (spherical correction),
$S_3=S+C/2$.

The above arithmetic operations are performed by the arithmetic device 22 on the data, such as a preoperative corneal shape of the patient's eye and a corrected refractive power to be obtained, inputted with the use of the data input device 21.

For example, in the case where the correction amount of the refractive power is S=−1.0 D, C=−5.0 D and A=180°, the refractive power in each principal meridian direction is −6.0 D in a 90° direction and −1.0 D in a 180° direction. Here, an amount to be corrected in each step is calculated as follows.

(1) First step (hyperopic astigmatic correction)
$S_1=0$ D, $C_1=+2.5$ D and $A_1=90°$:
as the result of the hyperopic astigmatic correction, the thus obtained refractive power will be −6.0 D in a 90° direction and −3.5 D in a 180° direction.

(2) Second step (myopic astigmatic correction)

$S_2=0$ D, $C_2=-2.5$ D and $A_2=180°$:

as the result of the myopic astigmatic correction, the thus obtained refractive power will be −3.5 D in a 90° direction and −3.5 D in a 180° direction.

(3) Third step (spherical correction)

$S_3=-3.5$ D, which is a spherical equivalent of the correction amount of the refractive power.

By performing the three steps, the thus obtained refractive power will be 0 D in both principal meridian directions, which means that all the correction amount of the refractive power is done all the way. In addition, since the astigmatic correction is also effected by hyperopic astigmatic correction and the myopic astigmatic correction half-and half, the adverse effects of each correction are canceled, and therefore the both refractive power in each meridian between each principal meridian will be approximately 0 D.

Here, it should be noted that the order of performing each step is not limited as described above. Yet, it is preferable to first perform hyperopic correction which requires more precise alignment of the laser irradiation optical system with the patient's eye, and to perform myopic astigmatic correction proceeding to the spherical correction.

Hereinafter, another example will be described. In the case where the correction amount of the refractive power is $S=+4.0$ D, and $C=-8.0$ D and $A=90°$, an amount to be corrected in each step is calculated as follows:

(1) First step (hyperopic astigmatic correction)

$S_1=0$ D, $C_1=+4.0$ D and $A_1=180°$;

(2) Second step (myopic astigmatic correction)

$S_2=0$ D, $C_2=-4.0$ D and $A_2=90°$; and (3) Third step (spherical correction)

$S_3=0$ D, which does not need to be performed.

In the above examples, it is proffered to add a fourth step, after the corrective laser irradiation, of performing approximately uniform ablation for smoothing the laser irradiated surfaces. This ablation is achieved by a laser irradiation in a manner of PTK (phototherapeutic keratectomy) which is therapeutic superficial keratectomy. This ablation for smoothing is performed in the following manner.

First, upon limiting the ablation region, the opening region of the circular aperture 7 is set to a larger size than the region to be corrected. The laser beam irradiation is carried out in the same manner as the myopic correction: that is, the plane mirror 3 is moved stepwise so as to move the laser beam in a direction of the Gaussian distribution, and after each scanning, the image rotator 5 rotates so as to change the moving direction of the laser beam irradiation (into three directions at 120° intervals therebetween). As the result, the region limited by the circular aperture 7 is ablated approximately uniformly.

For example, in the case of performing corrective ablation on a zone of 5.5–6.5 mm, ablation for smoothing is performed on a region of 9.0 mm and at a depth of 30µ. At this time, the control device 20 controls the laser irradiation of the laser source 1 so as to make the repetition frequency of the laser pulse 10 Hz.

The smoothing ablation, in practice, is performed with instillation of an ophthalmic solution having low viscosity (sodium hyaluronic acid of low molecular weight). Since the ophthalmic solution pools in concaves in the corneal surface leaving convexes above the solution level, the laser beam irradiation onto the cornea in such a state ablates only the convexes as the concaves are masked by the solution. Consequently, the unevenness in the surface is reduced to make it smoother. The repetition-rate of the laser pulse is 10 Hz, which is quite slow, to allow time for the ophthalmic solution to be back in the convexes after it is scatted by the preceding pulse of the laser irradiation.

Still further, another example is described hereinafter. For example, in the case where the correction amount is $S=-6.0$ D, $C=-4.0$ D and $A=180°$, an amount to be corrected in each step is as follows:

(1) First step (hyperopic astigmatic correction)

$S_1=0$ D, $C_1=+2.0$ D and $A_1=90°$;

(2) Second step (myopic astigmatic correction)

$S_2=0$ D, $C_2=-2.0$ D and $A_2=180°$; and (3) Third step (spherical correction)

$S_3=-8.0$ D.

In this case, the ablation amount of the myopic correction is relatively large. That is, if the myopic astigmatism corrective ablation and the myopic corrective ablation are performed on a zone of the same size, the ablation depth at the center portion tends to be too deep.

To avoid the above situation, a multi-zone is applied to the second step so as to differentiate the size stepwise. To differentiate the size, the optical zone is denoted by OZ (mm) while the transition zone is denoted by TZ (mm), and then the size of the transition zone is obtained in the expression, TZ=OZ+2.0 mm. Then, the diameter of the irradiation is enlarged by 0.5 mm at every astigmatic correction amount of −0.5 D. The myopic correction of the spherical component is performed on the same size at every −1.0 D.

In the case of the above example, the spherical correction (the myopic correction) for $S_3=-8.0$ D, and the myopic astigmatic correction for $C_2=-2.0$ need to be effected. So, correction for $S_2=-1.0$ D, $C_2=-0.5$ D and $A_2=180°$ is performed on the following four sizes (the spherical correction for $S_2=-1.0$ D and the myopic astigmatic correction for $C_2=-0.5$ D and $A_2=180°$ are performed separately):

(1) OZ 6.5/TZ 8.5 mm;

(2) OZ 6.0/TZ 8.0 mm;

(3) OZ 5.5/TZ 7.5 mm; and (4) OZ 5.0/TZ 7.0 mm.

Thereafter, the rest of the spherical correction for $S_3=-4.0$ D is performed as the third step. As described above, by differentiating the size of the zone stepwise upon performing the myopic astigmatic correction (and simultaneously, the myopic correction), the ablation depth at the center is made generally shallow.

Here, in the above example, the first step of the hyperopic correction is performed under the condition where OZ 5.5/TZ 9.0 mm, and the third step of the spherical correction is performed under the condition where OZ 5.0/TZ 7.0 mm. Further, also in this case, the smoothing ablation should be performed as the forth step.

Data for differentiating the size with the use of multi zone as derived above is calculated by the arithmetic device 22 at the input of the data necessary for correction of the patient s eye from the data input device 21. The control device 20 contains a program for performing the ablation for hyperopic astigmatic correction, myopic astigmatic correction, spherical correction and for smoothing in sequence. In addition, the control device 20 controls each device based on the control data for laser irradiation obtained from the arithmetic result and the inputted data upon carrying out the laser irradiation. The gradual change of the optical zone and the transition zone is achieved by controlling the opening region of the circular aperture 7. For the details of the way to form the transition zone, see U.S. Pat. No. 5,445,633.

As described above, the present invention eliminates the need to obtain the hyper shift rate upon astigmatic correction as an empirical value. In addition, the present invention enables astigmatic correction with reducing the effect of change that the spherical component undergoes without any limitation of a specified correction range.

Further, the program for differentiating the size according to the correction amount upon the myopic astigmatic correction and also the program for smoothing ablation after the laser beam irradiation for effecting the correction is added to the sequence of the procedure. This eliminates the need to input data for each correction and therefore input errors are prevented allowing to perform surgery efficiently.

In the above embodiments, the so-called slit scanning method is applied as the laser irradiation method. Yet, the following methods are also applicable as an ablation method for correcting astigmatism by ablating the cornea in a step-like shape symmetrically with respect to the astigmatic axis. The methods are the spot scanning method, the one-shot irradiation method, a modified method of the above three methods. For example, a modified method of the slit scanning method or the one-shot irradiation method is disclosed in U.S. Pat. No. 5,713,892. In this method, a laser beam irradiates a corneal surface via variable blades and the width of a slot and the diameter of an iris are varied as the laser is pulsed to produce toric ablation of the corneal surface. Another example is disclosed in EP 628298 which is a modification of the slit scanning method for hyperopic correction. In this method, the image of a variable aperture such as a variable width slit and a variable diameter iris diaphragm, is scanned in a preselected pattern to perform ablative sculpting of a corneal surface. The scanning is performed with a movable image offset displacement mechanism having a projection lens which is capable of effecting radial displacement and angularly rotation of the profiled laser beam exiting from the variable aperture.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for corneal surgery to correct a refractive error by ablating corneal tissue with a laser beam emitted from a laser source and delivered onto a cornea of a patient's eye with a light delivering optical system, the apparatus comprising:

irradiation area limiting means for limiting an irradiation area of the laser beam and for varying the irradiation area;

first control means for controlling the irradiation area limiting means so as to reduce an ablation amount as the laser beam irradiates further away from a flattest meridian of astigmatism whereby effecting astigmatic correction;

second control means for controlling the irradiation area limiting means so as to increase an ablation amount as the laser beam irradiates further away from a steepest meridian of astigmatism whereby effecting astigmatic correction; and arithmetic means for dividing a refractive power required for astigmatic correction into halves approximately equally so that an approximately half of the astigmatic correction is achieved by the first control means and the residual astigmatic correction is achieved by the second control means.

2. The apparatus for corneal surgery according to claim 1, wherein the irradiation area limiting means includes:

a circular aperture of which opening diameter is variable; and a slit aperture of which slit width is variable.

3. The apparatus for corneal surgery according to claim 2, wherein the irradiation area limiting means further includes:

beam rotating means for shifting a position of a boundary of the slit-shaped laser beam and rotating the laser beam being displaced from an axis of the patient's eye on the axis of the patient's eye.

4. The apparatus for corneal surgery according to claim 1, wherein the irradiation area limiting means includes:

a circular aperture of which opening diameter is variable;

a slit aperture of which slit width is variable;

boundary shifting means for shifting a position of a boundary of the slit-shaped laser beam; and beam rotating means for rotating the laser beam which is displaced from an axis of the patient s eye on the axis of the patient's eye, and the first control means approximately uniformly ablates an area limited by the slit aperture with the laser beam as well as changes the area limited by the slit aperture gradually.

5. The apparatus for corneal surgery according to claim 1, wherein the irradiation area limiting means includes:

a circular aperture of which opening diameter is variable;

a slit aperture of which slit width is variable;

boundary shifting means for shifting a position of a boundary of the slit-shaped laser beam; and beam rotating means for rotating the laser beam which is displaced from an axis of the patient's eye on the axis of the patient's eye, and the second control means controls the boundary position of the laser beam shifted by the boundary shifting means and rotation of the beam rotating means.

6. The apparatus for corneal surgery according to claim 5, wherein the boundary shifting means moves a mirror in parallel whereby moving the slit-shaped laser beam in a direction of its width, and the second control means repeats a process of rotating the slit-shaped laser beam limited by the circular aperture on the axis of the patient's eye by the beam rotating means with the laser beam being displaced to a different degree.

7. The apparatus for corneal surgery according to claim 5, wherein the boundary shifting means includes:

a projection lens for projecting the slit aperture being displaced from the axis of the patient's eye; and said slit aperture of which slit width is variable, and the second control means repeats a process of rotating the slit-shaped laser beam limited by the circular aperture on the axis of the patient's eye by the beam rotating means with the laser beam being displaced to a different degree.

8. An apparatus for corneal surgery to correct a refractive error by ablating an optical zone of a cornea with a laser beam, the apparatus comprising:

input means utilized for inputting each data necessary for correction;

an optical system that includes
- a circular aperture of which opening diameter is variable,
- a slit aperture of which slit width is variable,
- a projection lens for projecting the apertures onto the cornea,
- a moving unit for making an area irradiated by the laser beam eccentric with respect to a center of the optical zone, and
- a rotator for rotating the laser beam;

first control means for controlling the optical system so as to bring a longitudinal axis of the slit aperture into coincidence with a flattest meridian of astigmatism whereby gradually changing the slit width of the slit aperture so that the laser beam that passes through the circular aperture and the slit aperture ablates more amount as it is closer to the flattest meridian and less amount as it is farther from the flattest meridian;

second control means for controlling the optical system in a manner that a longitudinal axis of the slit-like laser beam in a rectangular shape, which is limited by the circular aperture, is made parallel to a steepest meridian of astigmatism whereby gradually changing an eccentricity amount of the laser beam so that the laser beam that passes through the circular aperture and the slit aperture ablates less amount as it is closer to the steepest meridian and more amount as it is farther from the steepest meridian; and arithmetic means for dividing amount of astigmatic correction into halves approximately equally on the basis of the inputted data so that an approximately half of the astigmatic correction is achieved by the first control means and the residual astigmatic correction is achieved by the second control means.

9. An apparatus for corneal surgery to correct a refractive error by ablating an optical zone of a cornea with a laser beam, the apparatus comprising:

input means utilized for inputting each data necessary for correction;

an optical system that includes
- a circular aperture of which opening diameter is variable,
- a slit aperture of which slit width is variable,
- a projection lens for projecting the apertures onto the cornea,
- a scan mirror for making the laser beam in a rectangular shape in a manner that it crosses the opening of either or both of the circular aperture and the slit aperture, and
- an image rotator for rotating the laser beam on an optical axis of the optical system;

first control means for controlling the optical system in a manner that the scan mirror makes the laser beam in the rectangular shape scan an area limited by the circular aperture having a diameter larger than that of the optical zone and by the slit aperture of which longitudinal axis is brought into coincidence with a flattest meridian of astigmatism whereby the slit width of the slit aperture is gradually changed after each scan;

second control means for controlling the optical system in a manner that a longitudinal axis of the laser beam in the rectangular shape, which is limited by the circular aperture having a diameter larger than that of the optical zone, is made parallel to a steepest meridian of astigmatism whereby gradually changing an eccentricity amount of the laser beam with respect to the steepest meridian by the scan mirror causes the laser beam to ablate more amount as it is farther from the steepest meridian; and arithmetic means for dividing an amount of astigmatic correction into halves approximately equally on the basis of the inputted data so that an approximately half of the astigmatic correction is achieved by the first control means and the residual astigmatic correction is achieved by the second control means.

* * * * *

UNITED STATES PATENT AND TRADEMARK OFFICE
CERTIFICATE OF CORRECTION

PATENT NO.   : 6,315,771 B1                                    Page 1 of 1
DATED        : November 13, 2001
INVENTOR(S)  : Paolo Vinciguerra et al.

It is certified that error appears in the above-identified patent and that said Letters Patent is hereby corrected as shown below:

Column 10, claim 4,
Line 24, "patient s" should read -- patient's --.

Column 12, claim 9,
Lines 18-19, "which longitudinal" should read -- which a longitudinal --.

Signed and Sealed this

Twelfth Day of March, 2002

Attest:

JAMES E. ROGAN
Attesting Officer                Director of the United States Patent and Trademark Office